United States Patent

Vandenbooren et al.

[11] Patent Number: 5,844,114
[45] Date of Patent: Dec. 1, 1998

[54] METHOD FOR THE SELECTIVE HYDROGENATION OF A DINITRILE COMPOUND

[75] Inventors: Franciscus H.A.M.J. Vandenbooren, Maastricht; Hubertus J.M. Bosman; Jan Van Der Spoel, both of Sittard, all of Netherlands

[73] Assignee: DSM N.V., Heerlen, Netherlands

[21] Appl. No.: 557,535

[22] Filed: Nov. 14, 1995

[30] Foreign Application Priority Data

May 14, 1993 [BE] Belgium ................................. 9300504
May 9, 1994 [WO] WIPO .......................... pct/nl94/00101

[51] Int. Cl.$^6$ ................................................. C07C 209/48
[52] U.S. Cl. ........................................... 564/490; 564/491
[58] Field of Search ...................... 564/490, 491

[56] References Cited

U.S. PATENT DOCUMENTS 5,097,073  3/1992  Abe et al. ................................ 564/493
5,254,738  10/1993  Koehler et al. ......................... 564/491

FOREIGN PATENT DOCUMENTS

A2 0 445 589  9/1991  European Pat. Off. .

OTHER PUBLICATIONS

Inui, et al., 'Effects of Seed Materials on a Zeolite and Its Performance of Methanol Conversion', Journal of Catalysis 79, 176–184 (1983).

Davis et al., 'Hydroformylation by Rhodium Zeolite A Catalysts', Journal of Catalysis 98, 477–486 (1986).

Mares et al., 'Preparation and Characterization of a Novel Catalyst for the Hydrogenation of Dinitriles to Aminonitriles', Journal of Catalysis 112, 145–156 (1988).

*Primary Examiner*—Brian M. Burn
*Attorney, Agent, or Firm*—Pillsbury, Madison & Sutro Cushman Darby & Cushman Intellectual Property Group

[57] ABSTRACT

The invention relates to a method for the selective hydrogenation of a dinitrile compound in the presence of a catalyst which comprises a metal of group 8 of the periodic system of the elements, the catalyst comprising a zeolite having a pore diameter of between 0.3 and 0.7 nm. The zeolite preferably has a structure chosen from the structures: ABW, AEI, AFT, ANA, ATN, ATV, ATT, AWW, BIK, CAS, CHA, DDR, EAB, EDI, ERI, GIS, JBW, KFI, LEV, LTA, MER, NAT, PHI, RHO, THO, YUG.

20 Claims, No Drawings

METHOD FOR THE SELECTIVE HYDROGENATION OF A DINITRILE COMPOUND

FIELD OF THE INVENTION

The invention relates to a method for the selective hydrogenation of a dinitrile compound in the presence of a catalyst which comprises a metal of group 8 of the periodic system of the elements. The 'periodic system of the elements' is understood to be the table represented on the inside of the cover of the Handbook of Chemistry and Physics, 58th Edition, CRC Press, 1977–1978.

BACKGROUND OF THE PRESENT INVENTION

Selective hydrogenation of dinitrile compounds makes it possible to obtain industrially interesting products in a simple manner. Complete hydrogenation of succinonitrile, for example, yields diaminobutane while partial hydrogenation yields aminobutyronitrile. Complete hydrogenation of adiponitrile for example yields hexamethylene diamine, while partial hydrogenation yields ε-amino-capronitrile. The invention relates to both complete and partial selective hydrogenation, which are usually carried out in the presence of a catalyst which comprises a metal of group 8 of the periodic system of the elements. Such a method, for the partial hydrogenation of dinitriles, is known from F. Mares, J. E. Galle, S. E. Diamond and F. J. Regina, Journal of Catalysis 112 (1988), pp. 145–156. According to this publication an alkane-dinitrile, such as ,ω-butanedinitrile (succinonitrile), is hydrogenated in the presence of a catalyst consisting of finely dispersed rhodium halogenide on a magnesium oxide carrier. The catalyst is pretreated with sodium hydroxide, which results in metallic rhodium on a magnesium oxide carrier. During the hydrogenation reaction an excess of $NH_3$, relative to the dinitrile, is supplied. In the hydrogenation of succinonitrile at a reaction temperature of 100° C., a pressure of 5 MPa and a reaction time of 5.5 hours a conversion of 89.4% and a selectivity towards aminobutyronitrile of 87.3% are realised. Although the conversion and selectivity are high, 11.9% of the succinonitrile is converted into dimers and oligomers. In the selective hydrogenation of dinitriles dimers, oligomers and tar-like compounds are undesired byproducts. Moreover, the formation of these undesired byproducts leads to a decrease in the activity of the catalyst.

From EP-A-445589 it is known to use a catalyst containing a metal of group 8 of the periodic system of the elements for the complete hydrogenation of dinitriles. According to EP-A-445589 a mixture of cobalt oxide and various metal oxides is used as a catalyst. Diamine yields of over 97% are obtained. During the reaction ammonia is added in a molar ratio of between 1:1 and 100:1, relative to the dinitrile. Although the yield of diamines is high, the process according to EP-A-0445589 has the disadvantage that high reaction pressures are used, namely 30 MPa in the examples. Because of this the reaction has to be carried out in heavy reactors. Moreover, because ammonia is added during the reaction, undesired dimers, oligomers and tar-like products are formed.

SUMMARY AND OBJECTS OF THE PRESENT INVENTION

It is the aim of the invention to provide a method for the hydrogenation of a dinitrile compound using a simple process, at a high reaction rate, with a high yield of desired products, wherein the formation of undesired byproducts is limited.

This is achieved according to the present invention by using a catalyst which comprises a zeolite having a pore diameter of between 0.3 and 0.7 nm. 'Pore diameter' is understood to be the smallest diameter of the largest channels in the zeolite. The channel diameters are based on the values as indicated in the Atlas of Zeolite Structure Types, 3rd revised edition, Ed. Butterworth-Heinemann, 1992.

According to the invention high yields of desired products such as diamines and amino-alkanenitriles are obtained. Moreover, with the method according to the invention there is no need to dose ammonia or other bases during the reaction. In addition, according to the invention it is possible to selectively prepare both completely and partially hydrogenated products with the aid of one catalyst, by varying the reaction conditions.

DETAILED DESCRIPTION OF THE INVENTION

According to the invention use is preferably made of a catalyst that comprises a zeolite having a structure with one of the following indications: ABW, AEI, AFT, ANA, ATN, ATV, ATT, AWW, BIK, CAS, CHA, DDR, EAB, EDI, ERI, GIS, JBW, KFI, LEV, LTA, MER, NAT, PHI, RHO, THO, YUG. The given structure indications are defined in the aforementioned Atlas of Zeolite Structure Types.

In particular the zeolite has a pore diameter of 0.3–0.5 nm according to the invention. Such a catalyst yields a very high selectivity and can be used in a wide temperature range.

The hydrogenation of the dinitriles according to the invention probably takes place substantially in the pores of the zeolite. According to the invention use is therefore preferably made of a zeolite with a large internal surface area. 'Internal surface area' is understood to be the area that is available for the adsorption of hydrogen per gram of catalyst. This area is determined with the aid of $H_2$-temperature programmed desorption ($H_2$-TPD) as described in J. A. Schwarz and J. R. Falconer, Catalysis Today, Vol. 7, No. 1, 27–30. In particular the internal surface area of the catalyst is at least 10 $m^2/g$, in particular at least 20 $m^2/g$. An internal surface area of more than 50 $m^2$ proves to be difficult to realise.

Since during the hydrogenation reaction the reactants do not only adsorb in the pores of the catalyst but also on the surface of the catalyst particles, reaction may also take place at the outer surface of the catalyst particles. These reactions at the outer surface of the catalyst particles may lead to the formation of undesired byproducts. Therefore, according to the invention, use is preferably made of a catalyst whose particles have an outer surface that has been rendered inert. An 'outer surface that has been rendered inert' is understood to be a surface to which the reactants and reaction products do not or do virtually not adsorb.

The outer surface may for example be rendered inert according to a known technique as described in: R. J. Davis, J. A. Rossin and M. E. Davis, Journal of Catalysis 98, 477–486 (1986). This publication describes a method for the selective poisoning of the outer surface of a zeolite catalyst, through a treatment with cyclohexyl-mercaptan. Another method that can be used is the complexation of the metal atoms of group 8 of the periodic system of the elements that are located at the outer surface. This can be done by using a complexing agent that is so large that it cannot penetrate into the pores of the zeolite. An example of such a complexing agent is ethylenediaminetetra-acetic acid (EDTA).

The method according to the invention is suitable for hydrogenating dinitrile compounds of such a size that they fit into the pores of the zeolite at the reaction temperature. In general these compounds will be dinitrile compounds whose smallest diameter is smaller than or equal to 0.7 nm.

In particular α,ω-alkanedinitriles are suitable for conversion using the method according to the invention. These alkanedinitriles have a general formula NC—$(CH_2)_n$—CN, where n is an integer between 0 and 12. Preferably n is an integer between 1–6. The following examples can be mentioned: malononitrile (n=1), succinonitrile (n=2), adiponitrile (n=4) and glutaronitrile (n=5). The method according to the invention is particularly suitable for the hydrogenation of succinonitrile and adiponitrile.

The hydrogenation of α,ω-alkanedinitriles can be represented in the following reaction scheme:

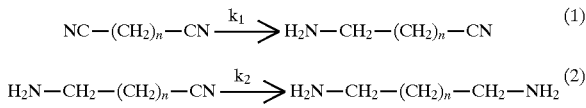

In this reaction scheme the products of reactions (1) and (2) are desired reaction products. The ω-aminoalkanenitrile formed in reaction (1) can react further under the influence of hydrogen to form diamines according to reaction equation (2). $K_1$ and $k_2$ represent the rate constants of reactions (1) and (2). With a selective hydrogenation to ω-aminoalkanenitrile the $k_1/k_2$ ratio is high. If a diamine is desired as a reaction product the reaction conditions are set so that the $k_1/k_2$ ratio is small. The reaction temperature has a strong influence on the $k_1/k_2$ ratio.

According to the invention the reaction temperature is generally between 70° and 200° C. At temperatures above 200° C. the formation of byproducts may increase considerably, whereas at temperatures below 70° C. the conversion proceeds too slowly. At higher temperatures the $k_1/k_2$ ratio decreases. Dependent on the catalyst used, mainly aminoalkanenitriles are formed at for example 70°–110° C., whereas the formation of diamines increases at temperatures of 110°–140° C. In addition to this, the formation of ring products (for example pyrrolidine) also increases at higher reaction temperatures.

The different reaction products can be separated using simple and known methods, for example by means of distillation.

For the hydrogenation reaction the dinitrile may be dissolved in a suitable solvent. The solvents that may be used according to the invention should be chosen in such a way that both the initial reactants and the reaction products dissolve in the solvent. Examples of suitable solvents are: tetrahydrofuran, dioxane, alkane(di)amines, alcohols and ethers. Particularly suitable solvents are the α,ω-alkanediamines or alcohols having 1–10 C atoms. Examples of such particularly suitable solvents are diaminoethane, diaminobutane, diaminohexane, methanol, ethanol, n-propanol, i-propanol and n-butanol.

Hydrogenation is generally carried out with the aid of hydrogen gas ($H_2$). Hydrogen is usually present as a gas phase, which is in contact with the solution containing the dinitrile, whereby a small portion of the hydrogen gas usually dissolves in the solution. The hydrogen partial pressure is at least 1 atm (0.1 MPa); usually, however, hydrogen pressures of 5–500 atm (0.5–50 MPa), in particular 30–100 atm (3–10 MPa), are used. These and all other pressures are given as absolute pressures. Other gases may be present during the reaction, but the amounts of such gases are usually small.

During the reaction hydrogen is preferably present in a $H_2$:dinitrile molar ratio of at least 1. The hydrogen that is consumed in the reaction is usually suppleted in the course of the reaction. Usually the hydrogen pressure is kept more or less constant during the entire course of the reaction.

The optimum amount of catalyst used in the hydrogenation is dependent on the type of reactor used and the reaction conditions. A person skilled in the art will be able to determine the suitable amount of catalyst for every desired reactor in a simple manner. In general the amount of catalyst is such that the metal of group 8 is present in a ratio of 0.001–10 mol. %, relative to the amount of dinitrile.

The products that can be prepared according to the invention are widely used as starting materials for the chemical and pharmaceutical industries. An example of the use of partially hydrogenated products is the use of aminobutyronitrile as a starting material for the preparation of γ-aminobutyramide (gabamide), having the formula $H_2N$—$(CH_2)_3$—$CONH_2 \cdot HCl$, which is used for the preparation of antidepressants. Aminobutyronitrile can furthermore be converted into pyrrolidone through saponification and ring closure. ω-aminoalkanenitriles can also be used as starting materials for the production of nylons. ε-aminocapronitrile for example can be used as a starting material for caprolactam, which is used as a starting material for nylon 6. In this route ε-aminocapronitrile is prepared from 1,4-dicyanobutane (adiponitrile) through selective hydrogenation according to the invention, whereafter the ε-aminocapronitrile is converted, through saponification into 6-aminohexanoic acid (ε-aminocaproic acid), which is then converted into caprolactam via a ring-closure reaction in which $H_2O$ is produced.

The completely hydrogenated products that can be prepared according to the invention have many possible industrial uses. Diaminobutane for example is a starting material for the preparation of nylon 4.6, 1,6-diaminohexane (hexamethylenediamine) is a suitable starting material for the preparation of nylon 6.6.

The ring products that can be prepared according to the invention are also used as starting materials in the chemical and pharmaceutical industries. Pyrrolidine for example can be used as a starting material for the preparation of photographic chemicals, polyurethane catalysts, rubber additives, softeners and pigments. Pyrrolidine can furthermore be used in the preparation of many pharmaceutical products such as buflomodil, bepridil, endralazine, rolitetracycline, fluoxymesteron, clemisole, vincamine, fendosal, tripolidine, pirmidic acid, rocyclidine and rifampicine.

EXAMPLES

The invention will further be illustrated in the examples and comparative experiments, without however limiting the invention thereto.

The reaction products were analysed using a Hewlett Packard $HP_{5890}$® type gas chromatograph, provided with a column (type number CP WAX 51) filled with polyethylene glycol and hydrogen as the carrier gas. Succinonitrile was analysed using a separate Chrompack® 428 A type gas chromatograph having a column with the composition: 5% phenyl, 95% methylpolysiloxane, type CP SIL 8 CB and nitrogen as the carrier gas.

Example I

Preparation of an Ni-ZSM34 catalyst

A ZSM34 zeolite was prepared as described in Inui, Journal of Catalysis 79, 176–184 (1983). A gel was prepared which had the following composition, expressed in molar ratios: Si/Al=9.5, Na/Al=5.8, K/Al=1.2. The organic template was tetramethylammonium hydroxide. This gel was heated to 190° C. in an autoclave with a volume of 750 ml. After cooling a precipitate was removed through filtration and was rinsed with water. The precipitate was contacted with a 2-M solution of ammonium nitrate at 180° C. and then with a 0.6-M nickel nitrate solution at 80° C. The precipitate was then calcined in the air at 540° C. for 3.5 hours. The yield was 15.5 g of Ni-ZSM34. The catalyst was pre-reduced for 1.5 hours at 800° C. and atmospheric pressure in a gas mixture of 10 wt.% $H_2$ in $N_2$. The $H_2$-TDP area of the catalyst was 22 $m^2/g$, the Ni content was 6.6 wt. %.

Hydrogenation of succinonitrile

A Parr type autoclave with a volume of 160 ml was used as reactor. The reactor was equipped with a closable drain incorporating a filter, which blocks the catalyst particles. The reactor was furthermore equipped with a dosing vessel with a volume of 50 ml. The dosing vessel was connected to the autoclave via a dosing pipe fitted with a valve. Both the reactor and the dosing vessel were provided with controllable heating and pressure control devices. The contents of the reactor could be stirred with the aid of a stirrer.

5 g of catalyst was introduced into the autoclave as a slurry in 90 g of diaminoethane. The autoclave was then brought to an $H_2$ pressure of 7 MPa and was heated to 100° C., while stirring (1800 rpm). 5 g of succinonitrile was dissolved in 10 g of diaminoethane and introduced into the dosing vessel. Then the valve in the dosing vessel was opened, as a result of which the contents of the dosing vessel were forced into the autoclave, after which the reaction took place in the autoclave, while stirring (1800 rpm).

After 6 hours the reaction was stopped by opening the valve in the drain of the reactor, as a result of which the contents of the reactor, with the exception of the catalyst, flowed out of the reactor. The product was analysed with the aid of gas chromatography. The degree of conversion of succinonitrile was 40%. The reaction product consisted of: 96 mol. % aminobutyronitrile and 4 mol. % diaminobutane. Formation of pyrrolidine or of tar-like reaction products was not detected. For the results see also Table 1.

Example II

Succinonitrile was hydrogenated as in Example I, at a reaction temperature of 110° C., a reaction pressure of 8 MPa and a reaction time of 23 hours. The results are given in Table 1.

Example III

Succinonitrile was hydrogenated as in Example I, at a reaction temperature of 140° C., a pressure of 8 MPa and a reaction time of 3 hours. The results are given in Table 1.

TABLE 1

The hydrogenation of succinonitrile with the aid of the catalyst Ni-ZSM-34, Examples I-III

| Example | I | II | III |
|---|---|---|---|
| Temperature (°C.) | 100 | 110 | 140 |
| Pressure (MPa) | 7 | 8 | 8 |
| Amount of catalyst (g) | 5 | 0.5 | 1 |
| Reaction time (h) | 6 | 23 | 3 |
| Degree of conversion (%) | 40 | 67 | 61 |
| Selectivity (mol.%) | | | |
| towards aminobutyronitrile | 96 | 73 | 60 |
| diaminobutane | 4 | 16 | 29 |
| pyrrolidine | 0 | 11 | 7 |
| other (heavy) products | 0 | 0 | 4 |

Example IV

Under the experimental conditions indicated for Example I adiponitrile was hydrogenated at a reaction temperature of 140° C., a reaction pressure of 7 MPa and a reaction time of 1 hour. The results are given in Table 2.

Example V

As in Example IV, adiponitrile was hydrogenated at a reaction temperature of 120° C., a reaction pressure of 8 MPa and a reaction time of 5 hours. The results are given in Table 2.

TABLE 2

The hydrogenation of adiponitrile with the aid of catalyst Ni-ZSM-34, Examples IV and V

| Example | IV | V |
|---|---|---|
| Temperature (°C.) | 140 | 120 |
| Pressure (MPa) | 7 | 8 |
| Amount of catalyst (g) | 5 | 3.7 |
| Reaction time (h) | 1 | 5 |
| Degree of conversion (%) | 65 | 67 |
| Selectivity (mol.%) | | |
| towards ε-aminocapronitrile | 40 | 100 |
| diaminohexane | 60 | 0 |
| other (heavy) products | 0 | 0 |

Example VI

Preparation of an Ni-SAPO-34 catalyst

An Ni-SAPO-34 catalyst was prepared as indicated in Inui, Appl. Cat. 58 (1990), 155–163. The gel that was prepared had the following composition:

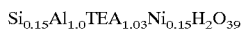

$Si_{0.15}Al_{1.0}TEA_{1.03}Ni_{0.15}H_2O_{39}$

The SAPO-34 gel formed was calcined and pre-reduced as in Example I. The $H_2$-TPD area of the catalyst was 19 $m^2/g$, the Ni content was 2.9 wt. %.

Hydrogenation of succinonitrile

Succinonitrile was hydrogenated as in Example I, at a reaction temperature of 120° C., a reaction pressure of 7 MPa and a reaction time of 3 hours. The degree of conversion was 17%; 74 mol. % aminobutyronitrile, 19 mol. % diaminobutane and 6 mol. % pyrrolidine were formed. No heavy reaction products were detected.

Example VII

Adiponitrile was hydrogenated with the aid of the Ni-SAPO-34 catalyst of Example VI as in Example I, at a reaction temperature of 110° C., a reaction pressure of 7 MPa and a reaction time of 2 hours. The results are given in Table 3.

Example VIII

Adiponitrile was hydrogenated as in Example VII, only the reaction time was 19 hours. The results are given in Table 3.

Example IX

Adiponitrile was hydrogenated with the aid of the Ni-SAPO-34 catalyst of Example VI as in Example I, at a reaction temperature of 125° C., a reaction pressure of 8 MPa and a reaction time of 3 hours. The results are given in Table 3.

Example X

Adiponitrile was hydrogenated as in Example VII, only the reaction time was 10 hours. The results are given in Table 3.

TABLE 3

The hydrogenation of adiponitrile with the aid of the Ni-SAPO-34 catalyst, Examples VII-X.

| Example | VII | VIII | IX | X |
|---|---|---|---|---|
| Temperature (°C.) | 110 | 110 | 125 | 125 |
| Pressure (MPa) | 7 | 7 | 8 | 8 |
| Amount of catalyst (g) | 4.5 | 4.5 | 0.5 | 0.5 |
| Reaction time (h) | 2 | 19 | 3 | 10 |
| Degree of conversion (%) | 11 | 25 | 32 | 75 |
| Selectivity (mol.%) | | | | |
| towards ε-aminocapronitrile | 100 | 71 | 79 | 62 |
| hexamethylenediamine | 0 | 29 | 21 | 38 |
| other (heavy) products | 0 | 0 | 0 | 0 |

We claim:

1. A method for the selective hydrogenation of a dinitrile compound in the presence of a catalyst which comprises a metal of group 8 of the periodic system of the elements, wherein said catalyst comprises a zeolite having a pore diameter of between 0.3 and 0.7 nm.

2. A method according to claim 1, wherein the zeolite has a structure selected from the group of structures consisting of ABW, AEI, AFT, ANA, ATN, ATV, ATT, AWW, BIK, CFAS, CHA, DDR, EAB, EDI ERI, GIS, JBW, KFI, LEV, LTA, MER, NAT, PHI, RHO, THO, and YUG.

3. A method according to claim 2, wherein the zeolite has a pore diameter of between 0.3 and 0.5 nm.

4. A method according to claim 1, 2 or 3, wherein the catalyst has an internal surface area of at least 10 m$^2$/g.

5. A method according to claim 1, 2 or 3 wherein the catalyst has an internal surface area of at least 20 m$^2$/g.

6. A method according to claim 1, 2 or 3, wherein the catalyst consists of catalyst particles having an outer surface that has been rendered inert.

7. A method according to claim 1, wherein the hydrogenation is carried out with the aid of hydrogen at a temperature of 70°–200° C. and a hydrogen partial pressure of 3–10 MPa.

8. A method for selectively hydrogenating an α,ω-alkanedinitrile which comprises at least partially hydrogenating the α,ω-alkanedinitrile the presence of a porous zeolite catalyst having a pore diameter of between 0.3 and 0.7 nm and a metal selected from the metals of group 8 of the periodic system of the elements said particles having an inert outer surface, said catalyst having an internal surface area of at least 10 m$^2$/gram catalyst to 50 m$^2$/gram catalyst.

9. A method according to claim 8, wherein said α,ω-alkanedinitrile is represented by the formula NC—(CH$_2$)$_n$—CN wherein n represents an integer between 0 and 12.

10. A method according to claim 8, wherein said pore diameter is 0.3–0.5 nm.

11. A method according to claim 8, wherein the zeolite has a structure selected from the group of structures consisting of ABW, AEI, AFT, ANA, ATN, ATV, ATT, AWW, BIK, CFAS, CHA, DDR, EAB, EDI ERI, GIS, JBW, KFI, LEV, LTA, MER, NAT, PHI, RHO, THO, and YUG.

12. A method according to claim 8, wherein said hydrogenation is effected in the presence of hydrogen at a temperature of 70°–200° C. at a hydrogen partial pressure of 3 to 10 MPa.

13. A method according to claim 8, wherein said pore diameter is 0.3 to 0.5 nm, and said zeolite has a structure selected from the group of structures consisting of ABW, AEI, AFT, ANA, ATN, ATV, ATT, AWW, BIK, CFAS, CHA, DDR, EAB, EDI ERI, GIS, JBW, KFI, LEV, LTA, MER, NAT, PHI, RHO, THO, and YUG.

14. A method according to claim 1 or 3, wherein the dinitrile Is at least one selected from the group consisting of succinonitrile and adiponitrile.

15. A method according to claim 8, wherein the αω-alkanedinitrile is at least one selected from the group consisting of succinonitrile and adiponitrile.

16. A method according to claim 1, wherein the hydrogenation is carried out with the aid of hydrogen at a temperature of 70°–100° C.

17. A method according to claim 1, wherein the hydrogenation is carried out with the aid of hydrogen at a temperature of 110° C. to 140° C.

18. A method according to claim 8, wherein the hydrogenation is carried out with the aid of hydrogen at a temperature of 70° C to 100° C.

19. A method according to claim 8, wherein the hydrogenation is carried out with the aid of hydrogen at a temperature of 110°0 C. to 140° C.

20. A method according to claim 1 or 8, wherein in the hydrogenation the a mount of catalyst used is such that the metal from group 8 of the periodic table is present in a ratio of 0.001–10 mol. %, relative to the amount of dinitrile.

* * * * *

UNITED STATES PATENT AND TRADEMARK OFFICE
CERTIFICATE OF CORRECTION

PATENT NO. : 5,844,114
DATED : December 1, 1998
INVENTOR(S) : VANDENBOOREN, et al It is certified that error appears in the above-identified patent and that said Letters Patent is hereby corrected as shown below:

Title page, --[63] Continuation of PCT/NL94/00101, May 9, 1994--

Column 1, line 5, after "FIELD OF THE INVENTION"

Insert --This is a continuation of PCT/NL94/00101, filed May 9, 1994--

Signed and Sealed this

Thirty-first Day of August, 1999

Attest:

Q. TODD DICKINSON

*Attesting Officer*   *Acting Commissioner of Patents and Trademarks*